US00PP21066P3

(12) United States Plant Patent
Chin et al.

(10) Patent No.: US PP21,066 P3
(45) Date of Patent: Jun. 15, 2010

(54) **MALE *ASPARAGUS* HYBRID PLANT 'NJ977'**

(50) Latin Name: *Asparagus officinalis*
Varietal Denomination: NJ977

(75) Inventors: Chee-kok Chin, Holmdel, NJ (US); Stephen A. Garrison, Pittsgrove, NJ (US); John J. Kinelski, Princeton, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 12/074,608

(22) Filed: Mar. 4, 2008

(65) Prior Publication Data

US 2009/0229026 P1 Sep. 10, 2009

(51) Int. Cl.
*A01H 5/00* (2006.01)

(52) U.S. Cl. ..... Plt./260

(58) Field of Classification Search ..... Plt./260
See application file for complete search history.

*Primary Examiner*—Kent L Bell
(74) *Attorney, Agent, or Firm*—James A. Lucas; Driggs, Hogg, Daugherty & Del Zoppo Co., LPA

(57) ABSTRACT

A male *asparagus* (*Asparagus officinalis*) hybrid denoted 'NJ977'. The plant has many desirable traits including vigorous plant growth, high yield, good resistance to rust (*Puccinia asparagi*) and good field tolerance to *asparagus* root and crown rot caused by *Fusarium oxysporum* and *Fusarium moniliforme*. These desirable traits have been shown to be transmissible to its progenies. The invention relates to plants and plant parts of 'NJ977' plant. The invention further relates to hybrid *asparagus* seeds and plants produced by crossing the male *asparagus* 'NJ977' plant with any female *asparagus* plant.

3 Drawing Sheets

Latin name of the genus and species: The Latin name is *Asparagus officinalis*.

Variety denomination: The varietal denomination is 'NJ977'.

BACKGROUND OF THE INVENTION

For an *asparagus* plant to be commercially viable and profitable, good yield is essential. It is well known that *asparagus* is susceptible to a number of diseases. Among the most devastating are rust caused by *Puccinia asparagi* d.c., (Kahn et al. 1952) and crown rot caused by *Fusarium oxysporum*, root rot caused by *Fusarium proliferatum* (syn = *F. moniliforme*) (Johnston et al., 1979; Guerrero et al., 1999). The presence of these diseases aversely impacts the yields and therefore the profitability of the product. Accordingly, resistance to these diseases is important to commercial success.

This invention herein described relates to a new and distinct *asparagus* hybrid, which was developed through crossing an elite female *asparagus* plant RF50 (Unpatented) selected from an old *asparagus* field with a homozygous male plant 22-34 (U.S. Plant Pat. 18387 P3). The performance of this hybrid has been evaluated for over 9 years in fields located near New Brunswick and Bridgeton, N.J. It is distinguished particularly as to its desirable traits of vigorous growth habit, higher yield, good field resistance to rust (*Puccinia asparagi*) and good field tolerance to root and crown rot (*Fusarium oxysporum*) and (*Fusarium moniliforme*).

BRIEF SUMMARY OF THE DRAWINGS

The color notations have been selected from observations as compared with the Munsell Limit Color Cascade. Colors are approximate as color depends on density of growth, horticultural practices, such as light level, fertilization rate, print resolution and other conditions and, therefore, the color characteristics of this new variety should be determined with reference to the observations described herein, rather than from this illustration alone. Furthermore, the coloration is not considered to be a distinguishing feature of this new variety.

DETAILED DESCRIPTION OF THE INVENTION

Figure 1:
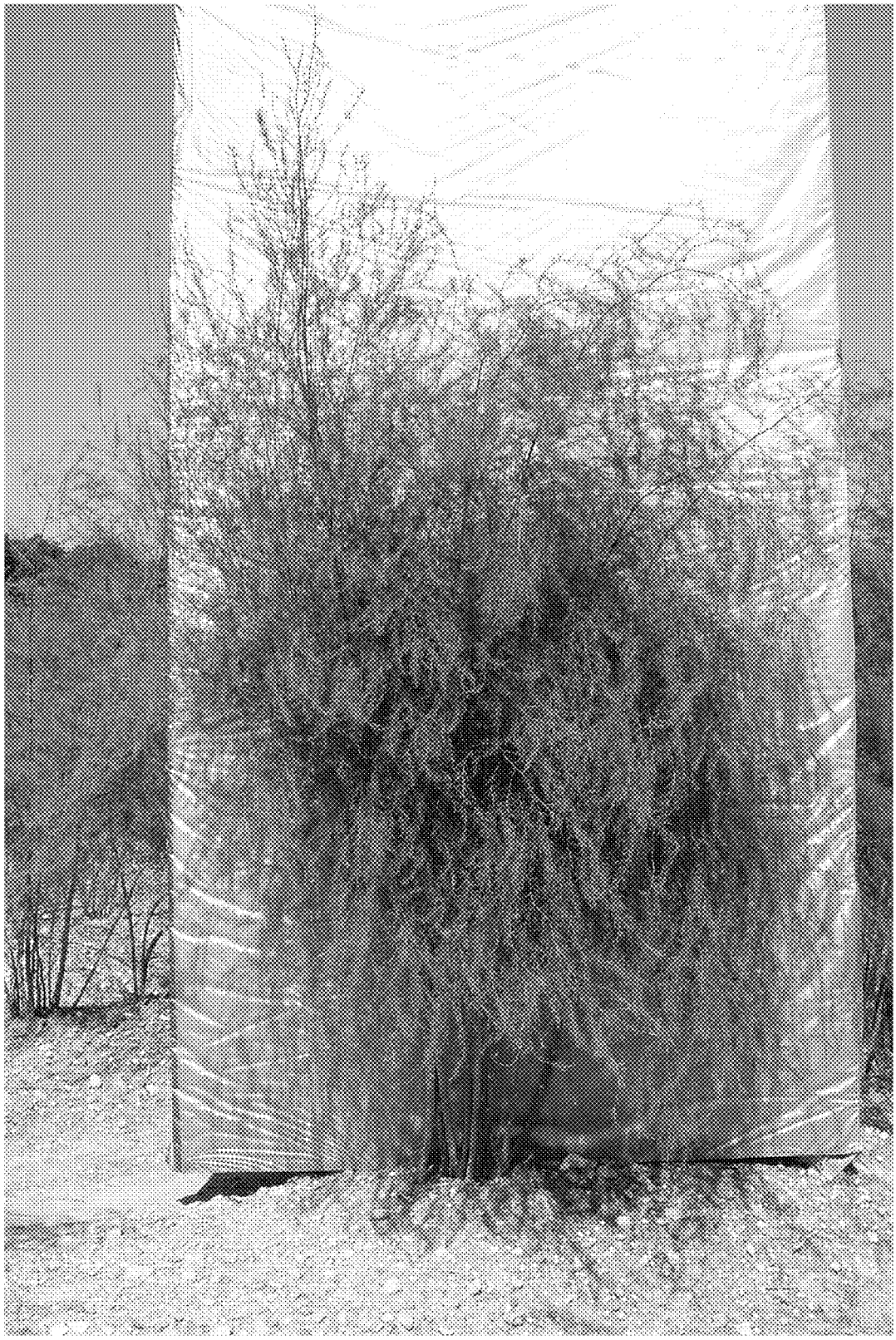
FIG. 1 shows in color a typical 'NJ977' plant of the new variety as it appears in a field under normal conditions.
Figure 2:
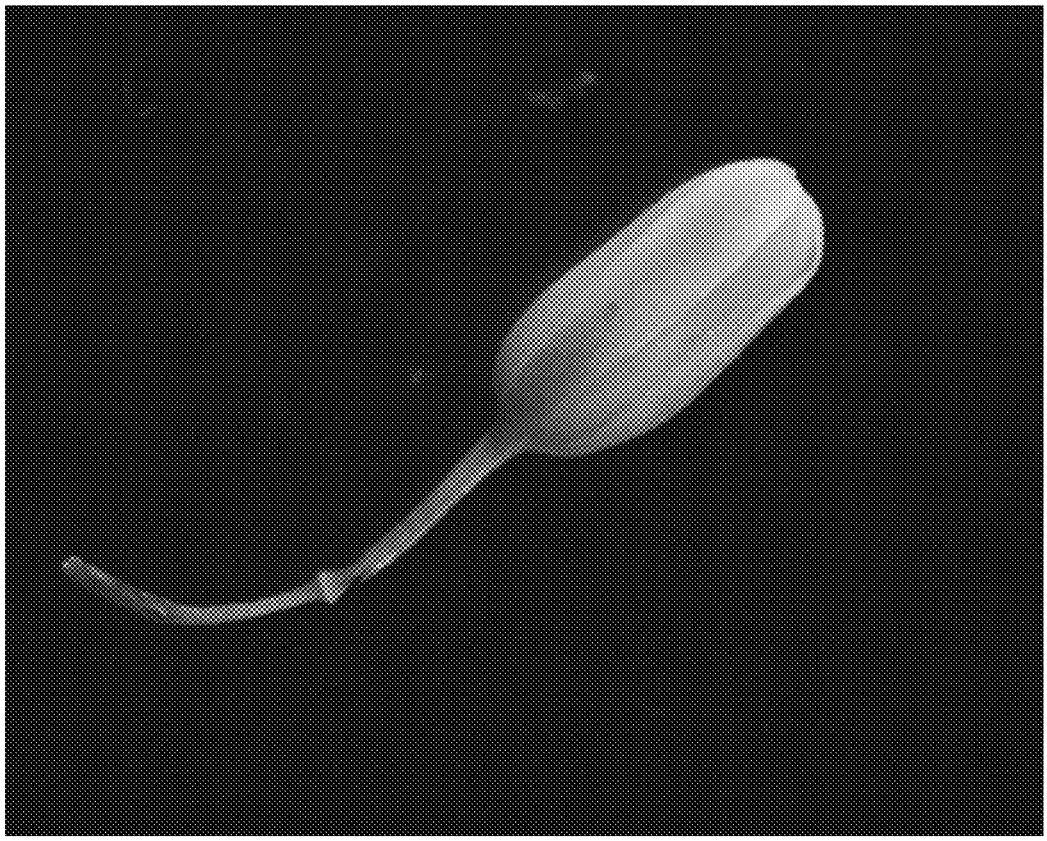
FIG. 2 shows in color a typical 'NJ977' flower as it appears in a field under normal conditions.
Figure 3:
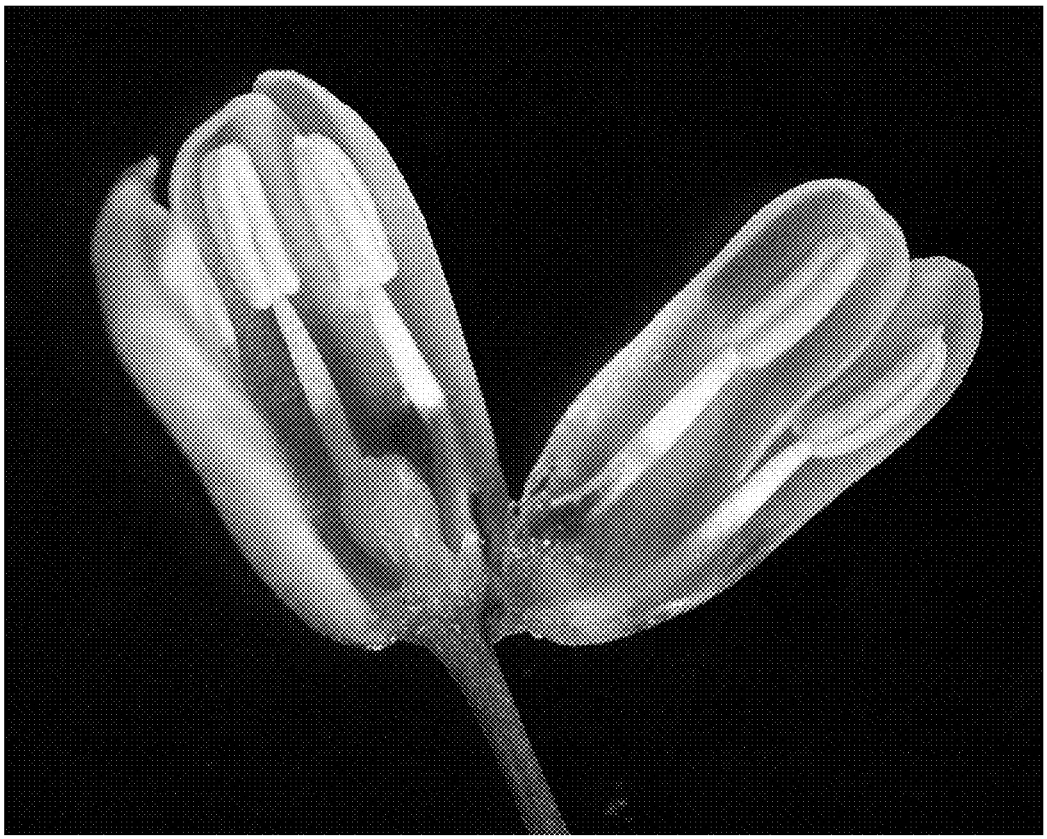
FIG. 3 shows in color a cut-open view of a typical 'NJ977' flower.

An extensive program of *asparagus* plant development, carried out in in trial fields in the vicinity of New Brunswick, and Bridgeton, N.J., to compare a large number of new hybrids and many of the commercially available elite hybrids including Jersey Giant, Jersey Knight has resulted in the identification of 'NJ977' as an *asparagus* hybrid with many desirable traits.

*Asparagus* (*Asparagus officinalis* Linn.) is a dioecious species with individual plants being either male or female in sex. In addition to differences in morphology, 'cultivars' may also differ in local adaptation, yield, disease resistance, and longevity. Desirable cultivars are developed by crossing of elite male and female parents. Both male and female parents transmit traits such as disease resistance, yield, and spear morphology to their progenies. This invention relates to new and distinct *asparagus* hybrid designated as 'NJ977'. Disease resistance of the kind found in the 'NJ977' plant will allow growers to plant the hybrid where rust, *Fusarium*, and stem blight now prevent profitable culture of the susceptible varieties.

*Asparagus* can be clonally propagated by crown division. Crown is the structure where shoots and roots join together.

Division or separation at the crown area will allow the propagation of *asparagus*. When propagated by crown division, successive generations of 'NJ977' have similar morphological appearance and possess the same desirable characteristics as the original 'NJ977' plant.

*Asparagus* can also be clonally propagated by tissue culture. An *asparagus* shoot tip or meristem when cultured on appropriate nutrient medium and appropriate conditions can grow, develop, and regenerate into a plant. Also, *asparagus* plant parts such as a spear segment when cultured on appropriate nutrient medium and appropriate conditions can grow, develop, and regenerate into an *asparagus* plant. Such plant can be efficiently divided and multiplied in appropriate nutrient medium. Successive generations of a 'NJ977' plant propagated by such tissue culture has been found to retain the same desirable characteristics as the original 'NJ977' plant.

When crossed with different male plants, *asparagus* 'NJ977' can transmit many of its desirable traits including vigorous growth habit, higher yield, desirable spear morphology, good levels of resistance to rust (*Puccinia asparagi*) and field tolerance to root and crown rot (*Fusarium oxysporum*) and (*Fusarium moniliforme*) to its progenies.

The following table shows that in yield and disease resistance the progenies of 'NJ977' compare very favorably to Jersey Giant (Plant patent #6624) and Jersey Knight, (Plant patent #5551) two of most popular *asparagus* varieties in the world today.

TABLE 1

| | Jersey Giant | Jersey Knight | 'NJ977' |
|---|---|---|---|
| Yield, LB/Acre | 4737 | 4445 | 4619 |
| Rust resistance* | 5.9 | 7 | 7.5 |
| *Fusarium* tolerance | Tolerant | Tolerant | Tolerant |

Data was taken from a trial conducted at an agriculture research center located in Bridgeton, N.J. The trial was planted in 1999. The above data represents the average of the data collected from 3 to 7 year old plants between 2002 and 2006. Rust resistance*: 0: no resistance, 10: complete resistance

BOTANICAL DESCRIPTION

Data that distinguishes *asparagus* plant 'NJ977' from other *asparagus* varieties that have been internally developed, as well as *asparagus* plants that are known and available commercially in the markets have been accumulated and are presented below. The data (averages from 3 clones) is assembled in the following table:

TABLE 2

*ASPARAGUS* PLANT: 'NJ977'

Stalk data:

Number of nodes below first branch: 31.
Distance from crown to first branch: 78.95 cm.
Number of branches: 50.3.
Distance between first and last branch: 147.96 cm.

TABLE 2-continued

*ASPARAGUS* PLANT: 'NJ977'

Number of cladophyll nodes beyond last branch: 34.67.
Length beyond last branch: 20.74 cm.
Length of longest headed stalk: 241.65 cm.
Largest stalk diameter: 20.33 mm.
Mean diameter of three largest stalks: 17.91 mm.
Number of stalks: 32.
Mature stalks color, bloom removed: Color 22-10.

Flower data:

All vegetative and reproduction parts glabrous and appearing non-glandular.
Number of flowers per cluster: observed 1-4, typically 2.
Tepals Observed: 6 in 2 whorls, forming campanulate corolla at anthesis, syntepalous for lowest 1 mm, free above, 5-6.5 mm long, 1.9-2.5 mm wide, dorsally slightly thickened,
apex outer surface margin color 24-2,
apex outer surface middle (vertical) color 23-9,
apex inner surface margin color 23-3,
apex inner surface middle (vertical) color 21-7,
base outer surface color 29-10,
base outer surface middle color 29-10,
base inner surface color 23-8,
base inner surface middle color 23-8,
Typical: straight in bud, recurved apically at anthesis, margin entire, strongly membranous; apex bluntly acute to obtuse, often twisted or crinkled after anthesis due to drying out of membranous area.
Flower width at midpoint: 2.6 mm.

Cladophyll data:

Average number per node: 5.1.
Shape: linear, filiform, needle-like; apex acute; base cunneate, margin-entire, color-21-11 throughout.

Leaf data:

Observed: Main stem leaves scale-like, triangular, at 15 cm to 30 cm from soil level leaves average 13 mm long, 12 mm wide at base, membranous: apex acuminate; base truncate; margin hyaline; Color-28-10 abaxial; 27-10 adaxial.
Terminal branch leaves scale-like, triangular, average 3 mm long, 1.5 mm wide at base, membranous; apex acuminate; base truncate; margin erose, hyaline. Color: 26-9 abaxial; 26-8 adaxial.
Typical: Bracts subtending inflorescence branches triangular, scale-like, membranous, especially towards margins, not keeled or winged, with small hanging appendix from dorsal midvein close to stem; margins entire; apex acute.

Reproductive Organs

Stamens- 6 in number, each stamen fused to middle of inner side of the base a tepal; length: 4.5-5.5 mm.
Filaments-filiform, slightly widened towards base, 3-3.6 mm long, 0.2-0.35 mm wide, about 0.4-0.5 mm wide at base.
Anthers elliptic, longitudinally dehiscent, introse to slightly latorose, base sagittate to widely triangular, basifix about 1.8 mm long and about 0.65 mm wide at base.
Rudimentary Gynoecium- rudimentary, tricarpellate, with barely visible sutures along ovary.
Rudimentary Ovary sessile, elliptic to obovate, 1.8-2.4 mm long, 1.3-1.6 mm wide at anthesis, color 21-11; style 1, rudimentary, barely noticeable, color 24-6; Stigma absent.

What is claimed is:

1. A new and distinct male *asparagus* hybrid plant 'NJ977' as herein shown and described.

* * * * *